United States Patent [19]

Toukan et al.

[11] Patent Number: 4,618,438

[45] Date of Patent: Oct. 21, 1986

[54] POLYMERIC THIADIAZOLE LUBRICANT ADDITIVE

[75] Inventors: Sameeh S. Toukan, Chester; James P. King, Lansdale, both of Pa.

[73] Assignee: Pennwalt Corporation, Philadelphia, Pa.

[21] Appl. No.: 719,596

[22] Filed: Apr. 3, 1985

[51] Int. Cl.[4] .............................................. C10M 1/38
[52] U.S. Cl. .................................................. 252/47.5
[58] Field of Search ........................................ 252/47.5

[56] References Cited

U.S. PATENT DOCUMENTS

| 4,246,126 | 1/1981 | Arakelian et al. | 252/47.5 |
| 4,301,019 | 11/1981 | Horodysky et al. | 252/47.5 X |
| 4,410,703 | 10/1983 | Okorodudu | 252/47.5 X |
| 4,432,847 | 2/1984 | Fields | 252/47.5 X |
| 4,517,104 | 5/1985 | Bloch et al. | 252/47.5 X |

Primary Examiner—Ferris H. Lander

[57] ABSTRACT

Method of preparing an oil soluble lubricant additive composition which includes forming a stable reaction product of a polymer of 3,5-dimercapto-1,2,4-thiadiazole, a polyalkylene succinimide, a fatty acid, and a mercaptan of 8 to 15 carbon atoms.

23 Claims, No Drawings

POLYMERIC THIADIAZOLE LUBRICANT ADDITIVE

BACKGROUND OF THE INVENTION

This invention relates to oil soluble complexes prepared by the reaction of 1,2,4-thiadiazole dimercaptan polymer with a succinimide derivative containing an alkenyl group. A fatty acid and an aliphatic mercaptan can also, optionally, be included to provide enhanced results in certain applications.

Polymers of dimercaptothiadiazoles are known to be insoluble in either hydrophilic or oleophilic media. A method by which 1,3,4-thiadiazole dimercaptan is made oil soluble by reacting it with oil dispersible materials such as a succinimide derivative, or with polysulfides, mercaptans or amines containing at least one primary or secondary amine group is taught in U.S. Pat. No. 4,246,126.

The novel oil soluble complex composition of this invention differs from that of U.S. Pat. No. 4,246,126 in that it has better performance and its solubility increases significantly with mercaptans but decreases when reacted with polysulfides or amines.

The invention also provides a process for the preparation of oil soluble complexes of 3,5-dimercapto-1,2,4-thiadiazole polymer. This process is also applicable to the 1,3,4- and 1,2,3-thiadiazole polymer isomers.

The precise chemical nature of the composition of this invention is not known. However, it is certain that a chemical reaction takes place to produce a definite composition, hereinafter called "complex".

BRIEF SUMMARY OF THE INVENTION

The composition of the invention is described as an oil soluble lubricant additive comprising a stable, reaction product of the following reactants:

(a) a polymer of 3,5-dimercapto-1,2,4-thiadiazole; and (b) a polyalkylene succinimide having an alkenyl group of 50 to 100 carbon atoms in an amount of about 0.75 to 5.0 parts by weight of succinimide per part of the thiadiazole, and preferably 0.75 to 2.0 parts.

It is preferred that the polyalkylene succinimide of (b) has the structural formula:

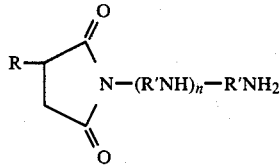

wherein R' is an alkylene radical of one to six carbon atoms, R is an aliphatic hydrocarbon having 50 to 100 carbon atoms, and n is a whole number from 0 to 8. Preferably, R' is ethylene or propylene and n is an integer of 1 to 3. R is preferably a polyisobutylene having an average molecular weight within the range of 700 to about 1400.

The reaction product can preferably include the following two additional reactants: an aliphatic carboxylic acid in an amount of from about 0.3 to 0.75 parts of acid per part of thiadiazole and a mercaptan having 8 to 15 carbon atoms present in an amount of about 0.5 to 1.5 parts of mercaptan per part of thiadiazole.

The aliphatic, fatty acid preferably has 8 to 20 carbon atoms. The mercaptan is preferably an aliphatic mercaptan having 8 to 15 carbon atoms and 1 or 2 mercapto groups.

The reaction product can be diluted with an oil diluent of vegetable or petroleum origin.

The lubricant of the invention comprises a major amount of a lubricating oil and about 1% to 10% by weight of the oil soluble additive as above described.

The method of the invention is defined as a method of preparing an oil soluble additive which comprises heating a mixture of a polymer of 3,5-dimercapto-1,2,4-thiadiazole and a polyalkylene succinimide having an alkenyl group of 50 to 100 carbon atoms, there being from about 0.75 to 5.0 parts by weight of succinimide per part of thiadiazole. The mixture of reactants is preferably heated at a temperature of about 125° to 175° C. for 1 to 4 hours. The mixture can also preferably include the fatty acid and mercaptan as described above.

DETAILED DESCRIPTION OF THE INVENTION

The succinimide derivative reactant is prepared by reacting a substituted succinic anhydride with a polyamine as taught by U.S. Pat. No. 3,202,678 to Stuart et. al (issued Aug. 24, 1965), the teachings of which are incorporated herein by reference:

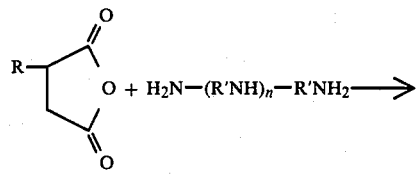

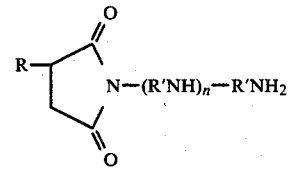

The substituted succinic anhydride is prepared by the reaction of maleic ahydride with a high molecular weight olefin. The method of preparation is well known in the art, as taught in U.S. Pat. No. 4,248,725 which is incorporated herein by reference. The high molecular weight olefin R substituent is an aliphatic hydrocarbon having a chain length of 50–100 carbon atoms, preferably a polyisobutylene having an average molecular weight of 1000. R can be an alkyl or an alkenyl radical.

The polyamines are alkylene amines wherein the alkylene radical (R') has 1–6 carbon atoms which form a straight or branched chain (preferably ethylene or propylene groups) and n has the value of 0–8 (preferably 1–3).

The fatty acid reactant can be of natural or synthetic origin. The acid can be saturated or unsaturated and has 8–20 carbon atoms, preferably 12–18 carbon atoms. Examples of such acids are: capric, lauric, palmitic, oleic, linoleic and stearic acids.

The mercaptans are preferably of the aliphatic type and can have straight or branched chain containing 1-2 mercapto groups, preferably one mercapto group, and 8-15 carbons, preferably 10-13 carbons. Octyl, nonyl, decyl, dodecyl, tert dodecyl and tetradecyl are examples of such mercaptans.

The polymer of 3,5-dimercapto-1,2,4-thiadiazole is prepared according to U.S. Pat. No. 4,107,059, the teachings of which are incorporated herein by reference.

The chemically inactive diluent can be a synthetic or natural oil, of vegetable or petroleum origin. Examples of such oils are corn oil, cotton seed oil, paraffin oil, ethylene polymer, 1-butene polymer, isobutene polymer, and saturated aliphatic hydrocarbons.

EXAMPLE 1

Preparation of an Oil Soluble Complex of 3,5-Dimercapto-1,2,4-thiadiazole Polymer A mixture of 168.0 g. of 3,5-dimercapto-1,2,4-thiadiazole polymer (U.S. Pat. No. 4,107,059) and 700.0 g. of a succinimide derivative (average molecular weight=1200–1400) is heated at 142°–148° C. for 5 hours followed by one hour heating at 160°–165° C. The reaction mixture is allowed to cool to about 150° C. before the addition of 532.0 g. of the diluent, a paraffinic mineral oil. Filtration is difficult and most of the reaction mixture is centrifuged without filtration for 2 hours at 2500 RPM to obtain 1,123.0 g. of a dark, viscous, oily liquid. The filtered portion is centrifuged to obtain 167.0 g. of the oily product. Total weight of the clear, dark product is 1,290.0 g. Total amount of sediment as a result of centrifuging is 94.0 g.

Analysis—Total sulfur content=3.98%.

Weld point of a sample of the above product is 620 kg. (EP properties—ASTM D 2596).

EXAMPLE 2

Preparation of an Oil-Soluble Complex of 2,5-Dimercapto-1,3,4-thiadiazole Polymer A mixture of 12% of 2,5-dimercapto-1,3,4-thiadiazole polymer (prepared by the oxidation of the disodium salt of 2,5-dimercapto-1,3,4-thiadiazole with hydrogen peroxide and phosphoric acid) and 50% of the succinimide derivative is heated at 142°–148° C. for 5 hours followed by one hour heating at 160°–165° C. The reaction mixture is cooled to 150° C. before the addition of 38% of the paraffinic mineral oil diluent. Centrifuging 47.2 g. at 2500 RPM for 2 hours yields 46.7 g. of a dark, viscous oil liquid. Weight of the sediment is 0.4 g.

Analysis—Total Sulfur content=5.69%.

The weld point of a neat sample is 400 kg. as compared to 620 kg. for the product of Example 1 (EP properties—ASTM D 2596).

Thus, even though the 1,3,4 isomer product of Example 2 contains more sulfur than the 1,2,4 isomer product of Example 1, it is inferior in performance properties.

EXAMPLE 3

Preparation of an Oil Soluble Complex of 3,5-Dimercapto-1,2,4-thiadiazole Polymer, Using 68% of the Succinimide Derivative Instead of 50%

The same procedure of Example 2 is followed except for the use of 68% of the succinimide to obtain a dark, viscous, oily liquid.

Analysis—Total sulfur content=3.94%, which is about the same as that for Example 1. Increasing the concentration of the succinimide did not further increase the oil solubility of the product.

EXAMPLE 4

Preparation of the Oil Soluble Complex of the Polymer of 3,5-Dimercapto-1,2,4-thiadiazole in the Presence of n-Dodecyl Disulfide Using the same procedure as in Example 2, and by reacting 12% of the polymer of 3,5-dimercapto-1,2,4-thiadiazole, 18% of n-dodecyl disulfide (prepared by the oxidation of n-dodecyl mercaptan with H$_2$O$_2$ in glacial acetic acid), 50% of the succinimide derivative and 20% of the paraffinic material oil diluent, there is obtained 90.4% of dark, viscous oily liquid which has a mild offensive odor and developed sediments on storage.

Analysis—Total sulfur content=7.45%, which indicates a slight increase in solubility. However, the increase is not significant because the oily solution continuously develops sediments on standing.

EXAMPLE 5

Preparation of the Oil Soluble Complex, Using a Polysulfide

Using the same procedure as in Example 2 and by reacting 12% of the polymer of 3,5-dimercapto-1,2,4-thiadiazole, 12% of tert. nonyl polysulfide, 50% of the succinimide derivative and 26% of the paraffinic mineral oil diluent, there is obtained 80.6% of very dark viscous oily liquid which develops significant amount of sediments on standing, in addition to 13% of residue left over in the centrifuge bottle.

Analysis—Total sulfur content=7.53%, an indication of poor solubility of the thiadiazole polymer complex since the polysulfide is high in sulfur content.

EXAMPLE 6

Preparation of the Oil Soluble Complex of the Polymer of 3,5-Dimercapto-1,2,4-thiadiazole in the Presence of Tert. Dodecyl Mercaptan The same procedure of Example 2 is followed except that after heating a mixture of the polymer of 3,5-dimercapto-1,2,4-thiadiazole (20%), tert dodecyl mercaptan (25%), and the succinimide derivative (50%) for 5 hours; the reaction mixture is heated at 160°–165° C. for 1¼ hours instead of one hour. After cooling to 150° C., the paraffinic mineral oil diluent (5%) is added and the reaction mixture is centrifuged for 2 hours at 2800 RPM to obtain a dark, viscous oily liquid.

Weld point of a neat sample of the product is 620 kg. (EP properties—ASTM D 2596). A paraffinic oil having 5% of the product provides a weld point of 315 kg.

Analysis—Total sulfur content is 12.6% which shows a significant increase in the solubility of the thiadiazole polymer complex with use of the mercaptan.

EXAMPLE 7

Preparation of an Oil Soluble Complex of the Polymer 2,5-Dimercapto-1,3,4-thiadiazole in the Presence of Tert. Dodecylmercaptan Example 6 is repeated using the same procedure and reactants except that the polymer of 2,5-dimercapto-1,3,4-thiadiazole is substituted for the polymer of 3,5-dimercapto-1,2,4-thiadiazole.

Weld point of a neat sample of the product is 500 kg. (EP properties—ASTM D 2596). A paraffinic oil with 5% of the product has a weld point of 250 kg.

Analysis—Total sulfur content=15.3%. In spite of the higher sulfur concentration (which would be expected to translate into enhanced lubricating properties), the performance is not as good as that of the product in Example 6.

EXAMPLE 8

Preparation of an Oil Soluble Complex of the Polymer 3,5-Dimercapto-1,2,4-thiadiazole in the Presence of n-Dodecylamine Example 7 is repeated using the same procedure and reactants except that n-dodecylamine 3,520%) is substituted for tert. dodecyl mercaptan (25%) and the quantity of the paraffinic mineral oil is increased to 10%. The resultant product is quite viscous and slow flowing. An additional 20% of the paraffinic mineral oil is added to obtain a dark, viscous, slow flowing oily liquid. After removing the oily product from the centrifuge bottle, there remains 14.6% of sediments mixed with small amount of product, indicating a very poor oil solubility of the polymer complex.

Analysis—Total sulfur content=4.93%.

EXAMPLE 9

By repeating Example 8 and substituting a tert. alkyl primary amine (for the n-dodecyl amine) having a highly branched alkyl chain of 18–22 carbons, there is obtained an almost identical product. Amount of sediments in centrifuge bottle is 12%. However, the finished product develops additional sediments on standing.

Analysis—Total sulfur content=5.39%, again indicating poor oil solubility of the polymer complex.

EXAMPLE 10

(a) Reproducibility of the Oil Soluble Polymer Complex 10.0 g. of the polymer of 3,5-dimercapto-1,2,4-thiadiazole
12.5 g. of tert. dodecyl mercaptan
25.0 g. of the succinimide derivative
2.5 g. of paraffinic mineral oil The first three of the above reactants are mixed and heated at 143°–148° C. for 5 hours. Thereafter, the temperature is raised to 160° C. and heating is continued for an additional 75 minutes. The paraffinic mineral oil is added and the reaction product is centrifuged while still hot for 2 hours at 2800 RPM. A very dark, viscous, oily product, weighing 45.3 g. is obtained. Less than 0.5 g. of a residue composed of a mixture of sediment plus small amount of product remains in the centrifuge bottle.

Weld point of 5% conc. in SAE 90 base oil is 315 kg. (EP properties—ASTM D 2596).

Analysis—C, 69.3%; H, 10.9%; N, 5.19%; $S_t$, 13.0%.

(b) Repetition of Experiment (a) As Is

Weld point of a 5% concentration in SAE 90 base oil is 315 kg.

Analysis—C, 69.2%; H, 11%; N, 5.29%; $S_t$, 13.3%.

(c) Repetition of Experiment (a) As Is

Weld point of a 5% concentration in SAE 90 base oil is 315 kg.

Analysis—C, 68.3%; H, 10.9%; N, 5.39%; $S_t$, 13.2%.

(d) Repetition of Experiment (a) As Is

Weld point of a 5% concentration in SAE 90 base oil is 315 kg.

Analysis—C, 68.2%; H, 10.8%; N, 5.23% $S_t$, 13.5%.

The above results indicate clearly that the oil soluble polymer complex of 3,5-dimercapto-1,2,4-thiadiazole has a definite composition.

EXAMPLE 11

Preparation of the Oil Soluble Complex of the Polymer 3,5-Dimercapto-1,2,4-thiadiazole in the Presence of Glyceryl Monooleate By following the procedure of Example 6 and reacting 20% of the polymer of 3,5-dimercapto-1,2,4-thiadiazole with 32% of glycerol monooleate, 24% of the succinimide derivative, 24% of tert. dodecyl mercaptan and without using the paraffinic mineral oil diluent, there is obtained a viscous dark, oily liquid.

Analysis—Total sulfur content=13.5% which indicates only a slight increase in the solubility of the polymer complex.

EXAMPLE 12

Preparation of the Oil Soluble Complex in the Presence of Oleic Acid

By repeating Example 11 and substituting oleic acid for glyceryl monooleate, there is obtained a dark, viscous oily liquid having greater oil solubility.

Analysis—Total sulfur content=11.9%.

EXAMPLE 13

Preparation of Polyisobutenylsuccinic Anhydride

A mixture of 92.0 g (0.1 mole) of polyisobutene (Indopol H-100 ac. m. wt. 920) and 19.6 g. (0.2 mole) of maleic anhydride is heated at 205°–210° C. for 24 hours. During the first 2 hours of heating, the temperature remains at about 205° C., thereafter the heating range is 205°–210° C. The reaction mixture is allowed to cool to about 80° C. before the addition of 150 ml. of heptane and, after stirring well, is filtered. The filtrate is stripped at about 55° C. and 10 mm. pressure and finally at 150°–170° C. for about one hour to remove any trace of unreacted maleic anhydride. Weight of the dark, reddish, viscous reaction product is 93.6 g. In addition, 11.2 g. of unreacted maleic anhydride is recovered.

Analysis—Neut. Equiv.=1,180. Acidity=0.84 m. eq./1 g. which corresponds to a molecular weight of 1,190.5.

EXAMPLE 14

Preparation of Polyisobutenylsuccinimide (a) A mixture of 100.0 g. (approximately 0.1 mole) of polyisobutenylsuccinic anhydride and 14.6 g. (0.1 mole) of triethylenetetramine (Aldrich Co.) is heated gradually over a period of one hour, up to 205° C. Vacuum of about 100 mm. pressure is applied and the heating is continued for an additional 0.5 hour at 205° C. More than 0.4 g. of water is collected. There is obtained 109.6 g. of viscous dark, almost non-flowing material containing a significant number of black particles suspending in the product. The imide derivative is used as is without filtration.

Analysis—C, 79.6; H, 13.6; N, B 4.37. N. Eq. (imide function)=1,488.

Infrared spectrum is consistent with the desired imide structure.

(b) The experiment is repeated using the same reactants and procedure except that only 11.0 g. of triethylene tetramine is used for each 100 g. of polyisobutenylsuccinic anhydride. There is obtained 107.2 g. of a very viscous dark yellowish brown, almost non-flowing material containing a significant number of black particles (but less than in case of Experiment part (a). Infrared spectrum is essentially the same as that of (a).

EXAMPLE 15

Preparation of the Oil Soluble Complex Using Polyisobutenylsuccinimide and a Vegetable Oil as Diluent (a) A mixture of polyisobutenylsuccinimide (Experiment 14(a); 25%); oleic acid (15%); polymer of 3,5-dimercapto-1,2,4-thiadiazole (20%); tert. dodecyl mercaptan (20%) and corn oil (20%) is heated for 4 hours at 142°–148° C. and for 1¼ hours at 160°–165° C. and worked up as in Example 10. There is obtained a dark, viscous oily liquid of good oil solubility.

Analysis—Total sulfur content=11%.

(b) Repeated Experiment (a) using same chemicals, procedure and quantities except cottonseed oil is substituted for corn oil to likewise provide a product of good oil solubility.

Analysis—Total sulfur content=11.2%.

EXAMPLE 16

Preparation of the Oil Soluble Complex Using a Polyisobutenylsuccinimide with Lower Amine Content A mixture of polyisobutenylsuccinimide (Experiment 14(b); 25%), oleic acid (10%); polymer of 3,5-dimercapto-1,2,4-thiadiazole (20%); tert. dodecyl mercaptan (20%) and cottonseed oil (25%) is heated and worked up as in Example 15. There is obtained a very dark viscous oily liquid of good oil solubility.

Analysis—Total sulfur content=12.1%.

EXAMPLE 17(a)

Preparation of Polyisobutenylsuccinic Anhydride: Boron Complex

A mixture of 36.0 g. of polyisobutenylsuccinic anhydride and 4.0 g. of boric acid is heated at 143°–148° C. for 4 hours. The initial heating causes slight foaming and a very mild reflux takes place in the thermometer adapter. A very viscous, almost non-flowing, yellowish brown reaction product is obtained.

Some crystalline material deposits on walls of reaction flask which is removed, washed with hexane and dried to weigh 1.6 g. It is slightly soluble in water and presumed to be boric acid or its derivative. It is discarded.

The viscous product develops a small but significant amount of light yellowish brown sediment on standing at room temperature.

Analysis—"B"=0.41%, equivalent to 2.3% boric acid.

EXAMPLE 17(b)

Preparation of the Oil Soluble Complex Containing Boron

Following the procedure of Example 15 and reacting polyisobutenylsuccinimide (20%), oleic acid (10%), polymer of 3,5-dimercapto-1,2,4-thiadiazole (20%), tert. dodecyl mercaptan (20%), the product of Example 17(a) (10%) and cottonseed oil (20%), there is obtained a very dark, viscous oily liquid.

Analysis—Total Sulfur content=11.4%. Boron=0.04% (Calc'd).

Weld point of a 5% concentration in SAE 90 base oil is 315 kg.

EXAMPLE 17(c)

Preparation of the Oil Soluble Complex Containing Boron

A mixture of the polymer of 3,5-dimercapto-1,2,4-thiadiazole (20%), succinimide derivative (30%), oleic acid (24%), tert. dodecyl mercaptan (24%), and boric acid (2%) is heated at 143°–148° C. for 4 hours, and at 160°–165° C. for 75 minutes. Reaction mixture is centrifuged for 2 hours at 2800 RPM to obtain a very dark, viscous, oily liquid.

Analysis—Total Sulfur content=11.7%. Boron=0.6%.

Weld point of a 5% concentration in SAE 90 base oil is 315 kg.

EXAMPLE 18

Incorporation of the Oil Soluble Composition of the Invention with Other Additives to Obtain Anti-wear, Anti-rust, Anti-corrosion, and Anti-oxidant Properties A mixture of the oil soluble product 71% (product of Example 15a), anti-wear additive (7.5%), anti-oxidant additive (10%), rust inhibitor additive (10%), and an anti-corrosion additive (1.5%) was heated until a uniform mixture is obtained.

A 5% solution of this mixture in SAE 90 base oil gives the following test results:

| Performance Data of a Gear Oil Additive Package Based on the Oil-Soluble Product According to This Invention. A Commercial Package is Used for Comparison | | | |
|---|---|---|---|
| Test | 5% of Gear Oil Additive Package in SAE 90 Base Oil | 7.5% of a Commercial Product[a] in SAE 90 Base Oil | MIL-L-2105C |
| EP Properties-ASTM D 2596 | | | |
| Weld pt., kg. | 315 | 315 | 300 |
| Load-Wear Index | 44.8 | 46.5 | 35 |
| Copper Corrosion-ASTM D 130 121° C. for 3 h | 1b[b] | 1b | 3 |
| Wear Prevention Characteristics ASTM D 2266 1800 rpm, 130° F. for 1 h; mm. | 0.30[c] | 0.38 | |
| Rust Inhibition-ASTM D 665B 24 h in synthetic sea water | Pass[d] | Pass | |
| Oxidation Stability-Oven Beaker Test - 150° C. | | | |
| Time for Viscosity to double | 5 weeks[e] | 5 weeks | |
| Sludge Formation after 48 h | light film | none | |
| Timken Value | 55 | — | 40 |

[a]A well known commercial industrial gear oil product which is a fully formulated package for MIL-L-2105C specification.
[b]Containing 0.075% of anti-corrosion additive.
[c]Containing 0.375% anti-wear additive, an oil soluble molybdenum complex.
[d]Containing 0.5% rust inhibitor.
[e]Containing 0.5% anti-oxidant, a phospherous compound.

EXAMPLE 19

Reation of the Oil Soluble Complex with Toluene Diisocyanate to Provide Enhanced Antiwear and Antioxidant Properties A mixture of 90.0 g. of the oil soluble complex, prepared as in Example 16, and 5.0 g. of 2,4-toluene diisocyanate is heated at 85° C. for 6 hours, under nitrogen atmosphere. There is no apparent change in the viscosity of reaction mixture and the infrared spectrum indicates that almost all the isocyanate has reacted. Another 5.0 g. of toluene diisocyanate is added and heating at 85° C. is continued for an additional 6.5 hours. Infrared spectrum indicates the presence of a significant amount of unreacted isocyanate. The temperature is raised to 140° C. and heating is continued for an additional 3.5 hours. Infrared spectrum indicates that the reaction of the isocyanate is complete.

There is obtained 94.4 g. of a very viscous, very dark, non-flowing material.

A 5% solution in SAE 90 base oil gives the following results:
Weld point—315 kg. (ASTM D 2596)
Wear scar—0.62 mm. (ASTM D 2266)
Load wear index—48.3 (ASTM D 2596)
Rust inhibition—Pass after 24 hours heating in synthetic sea water

EXAMPLE 20(a)

Evidence that the Oil Soluble Product is a Complex of Definite Structure

A mixture of 12% of the polymer 3,5-dimercapto-1,2,4-thiadiazole and 48% of the succinimide derivative is heated at 140°–150° C. for one hour. Thereafter, the temperature is raised to 170° C. and the heating is continued at 170°–175° C. for an additional hour. The paraffinic oil diluent (40%) is added and the reaction mixture is processed as in Example 10.

There is obtained a dark brown, viscous, oily liquid. Weight of the sediment is 4.0 g.

EXAMPLE 20(b)

Following essentially the procedure of Example 20(A) (above) and by reacting 15% of the above polymer instead of 12%, with 45% of the succinimide derivative, there is obtained a dark brown, very viscous, oily liquid. Weight of the sediment is 12.1 g.

(a) This shows that the oil additive according to the invention has a definite composition.

(b) If the mercaptan was present in the free state, then the product would have a very offensive odor, typical of free mercaptans.

(c) The thiadiaozle polymer is not soluble in water or in any organic or inorganic solvent. If it were present as such, in a suspension form, then on centrifuging at 2800 RPM for 2 hours, it should settle down. Therefore, it must be in a different soluble form.

(d) In Example 3, by using 68% instead of 50% of the succinimide derivative, a dispersing agent which has no sulfur, there was no increase in the amount of sulfur. If the oil soluble product was a mixture, an increase in the amount of suspending or dispersing agent should in turn increase the amount of the suspended sulfur-containing thiadiazole derivative.

(e) Reproducibility of the oil soluble product is excellent, as demonstrated by Example 10. This would not have occurred if the oil soluble product was composed of a mixture of chemicals. There would have been variation in the amount of sediment for each run, in the analysis and in the useful property.

(f) The active thiadiazole polymer is toxic to rabbits in the free state. If the oil soluble product was a mixture, then it should be also toxic to the rabbits. However, it was found not to be toxic.

We claim:

1. An oil soluble lubricant additive composition comprising a reaction product of:
    (a) a polymer of 3,5-dimercapto-1,2,4-thiadiazole; and
    (b) a polyalkylene succinimide having an alkenyl group of about 50 to 100 carbon atoms.

2. The composition as defined in claim 1 wherein the succinimide is present in an amount of about 0.75 to 5.0 parts by weight of succinimide per part of the thiadiazole.

3. The composition as defined in claim 1 having as additional reactants an aliphatic acid of 8 to 20 carbon atoms present in an amount of about 0.3 to 0.75 parts of acid per part of the thiadiazole and a mercaptan having 8 to 15 carbon atoms present in an amount of about 0.5 to 1.5 parts of mercaptan per part of thiadiazole, the succinimide being present in an amount of 0.75 to 2.0 parts of succinimide per part of the thiadiazole.

4. The composition as defined in claim 1 wherein the polyalkylene succinimide of (b) has the structural formula:

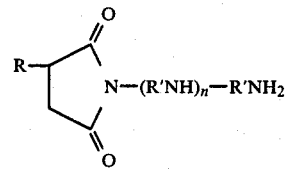

wherein R' is an alkylene radical of one to six carbon atoms, R is an aliphatic hydrocarbon having 50 to 100 carbon atoms, and n is a whole number from 0 to 8.

5. The composition as defined in claim 4 wherein R' is ethylene or propylene and n is an integer of 1 to 3.

6. The composition as defined in claim 5 wherein R is a polyisobutylene.

7. The composition as defined in claim 6 wherein the polyisobutylene has an average molecular weight within the range of 700 to about 1400.

8. The composition as defined in claim 3 wherein the aliphatic acid has 8 to 20 carbon atoms.

9. The composition as defined in claim 1 wherein in (b) the amount of succinimide is 1.0 to 1.3 parts of succinimide per part of the thiadiazole.

10. The composition as described in claim 3 wherein the aliphatic acid is present in an amount of 0.4 to 0.6 parts of the acid per part of the thiadiazole and the mercaptan is present in an amount of 0.75 to 1.2 parts of mercaptan per part of the thiadiazole.

11. The composition as defined in claim 3, 8, or 10 wherein the mercaptan is an aliphatic mercaptan having 8 to 15 carbon atoms and 1 or 2 mercapto groups.

12. The composition as defined in claims 1, 2, 3, 4, 5, 6, 7, 8, 9, or 10 having an oil diluent of vegetable or petroleum origin.

13. A lubricant comprising a major amount of a lubricating oil and about 1% to 10% by weight of the oil soluble composition of claims 1, 2, 3, 4, 5, 6, 7, 8, 9, or 10.

14. A method of preparing an oil soluble lubricant additive composition which comprises heating a mixture of a polymer of 3,5-dimercapto-1,2,4-thiadiazole and a polyalkylene succinimide having an alkenyl group of 50 to 100 carbon atoms, there being from about 0.75 to 2.0 parts by weight of succinimide per part of thiadiazole.

15. The method as defined in claim 14 wherein the heating is at a temperature of about 125° to 175° C. for about 1 to 4 hours.

16. The method as defined in claim 14 wherein the reactants include an aliphatic carboxylic acid in an amount of from about 0.3 to 0.75 parts of the acid per part of the thiadiazole.

17. The method as defined in claim 16 wherein the reactants include a mercaptan having 8 to 15 carbon atoms present in an amount of about 0.5 to 1.5 parts of the mercaptan per part of the thiadiazole.

18. The method as defined in claims 14, 15, 16, or 17 wherein the mixture is heated in a final heating stage for at least 30 minutes at a temperature of at least 160° C.

19. The method as defined in claim 17 wherein the reactants include a boron containing compound.

20. The method as defined in claim 19 wherein the boron containing compound comprises from about 0.04% to about 1%, as boron, by weight of the composition to provide a boron adduct.

21. The composition as defined in claim 3 wherein the additional reactants include an isocyanate compound to provide enhanced antiwear, antioxidant, and antirust properties to the composition.

22. The composition as defined in claim 21 wherein the isocyanate compound is a toluene diisocyanate.

23. The composition as defined in claims 21 or 22 wherein the isocyanate compound is added after the other reactants have substantially reacted.

* * * * *